US008497089B2

(12) United States Patent
Compagnone (10) Patent No.: US 8,497,089 B2
(45) Date of Patent: Jul. 30, 2013

(54) METHOD TO PREDICT TOXICITY USING THE ANALYSIS OF DYNAMIC ORGANELLE BEHAVIOUR

(75) Inventor: Nathalie Compagnone, Auriol (FR)

(73) Assignee: Innovative Concepts in Drug Development (ICDD), Meyreuil (FR)

( * ) Notice: Subject to any disclaimer, the term of this patent is extended or adjusted under 35 U.S.C. 154(b) by 400 days.

(21) Appl. No.: 12/675,494

(22) PCT Filed: Sep. 10, 2008

(86) PCT No.: PCT/EP2008/061969
§ 371 (c)(1),
(2), (4) Date: Feb. 26, 2010

(87) PCT Pub. No.: WO2009/034094
PCT Pub. Date: Mar. 19, 2009

(65) Prior Publication Data
US 2010/0311101 A1    Dec. 9, 2010

(30) Foreign Application Priority Data

Sep. 10, 2007 (FR) ..................... 07 06334

(51) Int. Cl.
*C12P 1/00* (2006.01)
(52) U.S. Cl.
USPC .......................... 435/41; 435/70.3
(58) Field of Classification Search
USPC .................. 435/41, 70.3
See application file for complete search history.

(56) References Cited

U.S. PATENT DOCUMENTS

| 6,716,588 B2 | 4/2004 | Sammak et al. |
| 2005/0002552 A1 | 1/2005 | Dunn et al. |

FOREIGN PATENT DOCUMENTS

| GB | 2 434 445 | 7/2007 |
| GB | 2 435 925 | 9/2007 |
| WO | WO 03/008536 | 1/2003 |
| WO | WO 2007/067809 | 6/2007 |

OTHER PUBLICATIONS

Minamikawa et al. "Chloromethyl-X-rosemine (MitoTracker Red) photosensitises mitochondria and induces apoptosis in intact human cells", J of Cell Science, 1999, 112:2419-2430.*
De Vos et al. "Tumor necrosis factor induces hyperphosphorylation of kinesin light chain and inhibits kinesin-mediated transport of mitochondria", The J of Cell Biology, 2000, 149(6):1207-1214.*
L929 fibroblast cell data sheet, 1 page 1999.*
Funk et al. "Effects of heat shock on the functional morphology of cell organelles observed by video-enhanced microscopy", The Anatomical Record, 1999, 255:458-464.*
Geisler, B. et al. "Video-Microscopic Analysis of the Cytotoxic Effects of Hydroxyethyl Methacrylate on Diploid Human Fibroblasts" in Vitro Toxicology, Nov. 4, 1995, pp. 369-375, vol. 8, No. 4, XP-009108576.
Maile, W. et al. "New Methods for Cytotoxicity Testing: Quantitative Video Microscopy of Intracellular Motion and Mitochondria-Specific Fluorescence" Molecular Toxicology, 1987, pp. 427-437, vol. 1, No. 4, XP-009108453.
Petronilli, V. et al. "Imaging the mitochondrial permeability transition pore in intact cells" *BioFactors*, 1998, pp. 263-272, vol. 8, XP-009108566.
Written Opinion in International Application No. PCT/EP2008/061969, Dec. 12, 2008, pp. 1-7.

\* cited by examiner

*Primary Examiner* — Susan Hanley
*Assistant Examiner* — Bin Shen
(74) *Attorney, Agent, or Firm* — Saliwanchik, Lloyd & Eisenschenk (57) ABSTRACT

The present invention provides an in vitro method to predict the effect of an exogenous element on an animal or human organism. This method is based on the analysis of variations of an organelle behaviour represented by at least two characteristics in isolated cells induced by the contact with the exogenous element and the determination of the cluster membership of the exogenous element which is representative of the effect of said element. Analyzed characteristics are selected from the group consisting of the motility, the morphology, the relationship with the cell cytoskeleton and the membrane permeability of said organelle. This method may be used to predict the efficacy or the toxicity of an element, such as a drug.

22 Claims, 4 Drawing Sheets

METHOD TO PREDICT TOXICITY USING THE ANALYSIS OF DYNAMIC ORGANELLE BEHAVIOUR

CROSS-REFERENCE TO RELATED APPLICATION

This application is the U.S. national stage application of International Patent Application No. PCT/EP2008/061969, filed Sep. 10, 2008, the disclosure of which is hereby incorporated by reference in its entirety, including all figures, tables and amino acid or nucleic acid sequences.

FIELD OF THE INVENTION

The present invention relates to the field of toxicology, particularly predictive toxicology

BACKGROUND OF THE INVENTION

To ascertain the safety of drugs under development, the pharmaceutical industry deploys a large amount of technology and process optimization to gain the ability of selecting and de-selecting drugs based on the criteria of therapeutic efficacy and potential of toxicity to the human health. This process is however not efficient, particularly because the potential of toxicity of drugs under development is not properly predicted by the current in vitro and in vivo models.

To date the evaluation of toxicity of a given substance relates to the use of animal models. Underlying is the assumption that toxic events observed in the animal are applicable and predictive of toxic events occurring in humans. The expression of animal toxicity data per dose at which toxicity is observed per body weight tends to undermine the occurrence of toxicity in humans. Moreover, the relatively low number of animals on which a substance is tested cannot predict for the occurrence of low frequency toxicity events that are shown in the human population. For example, a 0.01% incidence of toxicity in humans to a given substance means that approximately 25,000 to 250 million individuals are exposed to the given substance. To identify such a low occurrence toxicity in animals would require that 30 000 animals be exposed to the given substance. This being clearly impractical, exposure of fewer animals to high doses of a given substance is deemed desirable to identify hazards to human exposure to low doses.

The current drug development process only uses animal models to predict toxicity at a relatively late stage in drug development. The use of animal models would not be practical nor efficacious in generating toxicity data on the large number of substances found each year to have certain desirable therapeutic properties.

A significant need for alternative methods to predict toxicity exists.

Mechanistic approaches to model toxicity based on molecular mechanisms by which toxic event are expressed in humans have been pursued. Hence mitochondrial dysfunctions are studied in the context of pharmaco-toxicology using in vitro assays that describe one of the mitochondrial functions. These assays are used to measure acute, intrinsic toxicity of a given substance and are mostly based on the measure of oxidative phosphorylation in the several mitochondrial enzymatic complexes using either tissue biopsies, isolated mitochondria (Ishikawa et al., 2006), submitochondrial particles (Gustayson et al., 2002), or on the measure of cell ATP (Kerkela et al., 2006), or using cell viability assessment with the MTT test (Seok et al., 2007), or more recently on the measure of oxygen consumption using fluorescent or phosphorescent probes (Will et al., 2006).

The discovery that the mitochondrial membrane potential is essential to the normal functioning of mitochondria has led to the development of in vitro predictive assays to measure the effect of novel chemical entities on isolated mitochondria (Amacher, 2005). Similarly, observations that diseases affect mitochondrial motility has prompted the discovery of in vitro assays to identify substances that modify the changes in mobility induced by the disease in the hope of correcting the manifestations of the disease in humans (WO 2007/067809). However, these methods lack of predictivity and are hardly representative of the action of a tested substance on the entire mitochondria in its physiological context. Their use is limited to the screening of novel therapeutic substances or to the validation of a suspected mechanism of action of a therapeutic substance during its development.

Toxicity and lack of efficacy are currently the two main reasons for drug failure during development. Even though predictive toxicity data are acquired during the preclinical phases, 35 to 45% of the drug candidates fail due to unsuspected toxicity in humans. If some of the toxicity manifestations of a drug in development are seen during clinical trials, 20% of drugs among the 548 drugs approved by the food and drug administration (FDA) between 1975 and 1998, have caused toxic event of serious magnitude that motivated their change of label or market withdrawal. These facts raise the question of the efficacy of the current processes by which intrinsic, acute toxicity is assessed as a mean of predicting chronic or specific toxicities occurring in humans in the course of a therapeutic treatment.

Consequently, there is a strong need for early in vitro models that allow for a predictive assessment of the toxicity potential of substances, in particular for the ones with therapeutic properties during drug development.

SUMMARY OF THE INVENTION

The present invention provides a new in vitro method to predict the effect of an exogenous element on an animal or human organism comprising:

a) labelling at least one organelle contained in animal or human isolated cells;

b) contacting said isolated cells containing said at least one labelled organelle to said exogenous element;

c) determining variations of an organelle behaviour represented by at least two characteristics of said at least one labelled organelle in the presence of said exogenous element, said characteristics being selected from the group consisting of the motility, the morphology, the relationship with the cell cytoskeleton and the membrane permeability;

d) determining cluster membership of said exogenous element, clusters being established based on reference elements and said cluster membership being representative of the effect of said exogenous element on said organism.

BRIEF DESCRIPTION OF THE DRAWINGS

FIG. 7 illustrates the use of the method of the invention to predict the efficacy of a compound which is suspected to have an anti-age effect.

DETAILED DESCRIPTION OF THE INVENTION

Toxicity of mitochondrial origin is considered preponderant in explaining severe adverse reaction in post marketing pharmacovigilance analyses (Dykens et al., 2007). In order to avoid mitochondrial liabilities, routine screens need to be positioned within the drug-development process. Assays for mitochondrial function, cell models that better report mitochondrial impairment are needed to reduce the drug attrition rate. However, the current approach assessing molecular mechanism leading to mitochondrial dysfunction will only contribute partial results. The mitochondrial function cannot be reduced to, for example, the sole control of cellular oxidative phosphorylation or to the mutations of singular mitochondrial protein but represents a composite image of several individual molecular mechanisms, their interaction between each other and the interaction of the mitochondria with its cellular environment. Hence a linear analysis of these phenomenons is by nature reducing.

Considering that chronic toxicity is often resulting from a combination of cellular and more particularly mitochondrial dysfunctions, this toxicity can hardly be modeled by the study of a single of these dysfunctions.

In this context, the present invention proposes a method that is not limited by at least one of the previously described limitations, and particularly that allows for an evaluation of the efficacy and/or the toxicity of an exogenous element in a manner improved from the known art.

The inventors have discovered that analyzing multiple endpoints pertaining to organelle behaviour yield significant information to predict the effect of exogenous elements on animal or human organism.

The present invention considers the organelle as a system within the cell and described methods to analyze its functionality using a single readout measure defined through cluster analysis.

The readout measure discovered has been named "behaviour" as it relates to both the individual components of the organelle function such as the membrane permeability and the dynamic motility of the organelle inside a live cell through space and time but also considers elements of the interaction of the organelle with its cellular environment such as the dynamic relationship existing between organelle and elements of the cytoskeleton, or dynamic changes occurring in the organelle morphology.

The overall behaviour of the organelle is a dynamic measure of these different aspects within a live cell and is indexed to represent the ability of the organelle to adapt to disease, age or exogenous element to reflect the impact of either pathological conditions, normal ageing or exogenous elements capable of organelle impairment.

The measure of the organelle behaviour is essentially characterized by its inclusion of the labelling of at least one sub cellular organelle into live cells and the determination of the motility, the morphology, the relationship to cytoskeleton and the state of the permeability transition pore of at least one of the labelled organelles within the cells in its physiological or pathological state or put in contact with various concentrations of exogenous element in the aim of predicting the effect of such an element on animal or human organisms.

The method described in the invention considers the global functionalities of the organelle as represented by its behaviour and not solely the individual functions it carries that can be assessed for example studying organelle DNA synthesis, contribution of organelle function to cell viability as is currently available nor any of the isolated measures that are described herein. Even a combination of several analyses describing the isolated functions of the organelle does not recapitulate the whole functionalities of this organelle that are expressed in the phenotypic measures that describe of its behaviour.

This method thus offers a more sensitive and accurate technique than those currently existing to measure the impact of exogenous element, even at low doses.

The present invention provides an in vitro method to predict the effect of an exogenous element on an animal or human organism comprising:

a) labelling at least one organelle contained in animal or human isolated cells;

b) contacting said isolated cells containing said at least one labelled organelle to said exogenous element;

c) determining variations of an organelle behaviour represented by at least two characteristics of said at least one labelled organelle in the presence of said exogenous element, said characteristics being selected from the group consisting of the motility, the morphology, the relationship with the cell cytoskeleton and the membrane permeability;

d) determining cluster membership of said exogenous element, clusters being established based on reference elements and said cluster membership being representative of the effect of said exogenous element on said organism.

As used in this specification, the term "effect" refers to any phenomenon induced in the organism by the administration of or the contact with the exogenous element. In an embodiment, the exogenous element is intended to be used in therapeutically purposes and the tested effect is the therapeutic efficacy of this element, i.e. the achievement of the targeted result. In another embodiment, the tested effect is the toxicity of the exogenous element, i.e. the deleterious effect of this element on the organism.

In a preferred embodiment, the organism is a human organism.

The term "exogenous element", as used herein, is intended to be any type of manifestation that can be claimed to change the organism physiology. Such manifestation may be natural, chemical, biological or physical. Thus, the exogenous element may be any physical, chemical or biological element such as a physical particle, a wave or a chemical or biological substance.

In a particular embodiment, the exogenous element is selected from the group consisting of a drug authorized to be marketed, a biological or chemical substance with therapeutic potential, a biological or chemical substance contained in drugs, fertilizers, phytochemical products, food, cosmetic products and/or environmental toxicants. The exogenous element tested with the method of the invention may be already approved drugs, commercialized products or products in development from the pharmaceutical, chemical or cosmetic industry, chemical substance, biological entities, excipients, particles or wave of various origins entering the composition of medications, chemical products, fertilizers, and other phytochemical products, food, food supplements, nutraceuticals, cosmetic products or environmental toxicants.

The method of the invention comprises several steps as defined above.

The first step of this method, namely step a), consists of labelling at least one organelle contained in isolated cells of an animal or human organism.

The term "organelle" as used herein refers to any structure within the cell which has a specific function and is separately enclosed within its own lipid membrane.

In an embodiment, the organelle is selected from the group consisting of mitochondria, vesicles, peroxisomes, lysosomes, endoplasmic reticulum and vacuoles.

Preferably, the organelle is selected from the group consisting of mitochondria, vesicles and peroxisomes. More preferably, the organelle is mitochondria.

In an embodiment, one organelle is labelled, preferably mitochondria.

In another embodiment, several organelles are labelled, preferably mitochondria and vesicles, mitochondria and peroxisomes, vesicles and peroxisomes or mitochondria, vesicles and peroxisomes.

Preferably, several of each selected organelle are labelled per cell.

The labelling of at least one organelle can be performed using any method known by the skilled person. Preferably, the labelling is performed using a marker emitting fluorescent or luminescent signal.

In an embodiment, the labelling of an organelle is performed using a fluorochrome or a fluorescent probe specific of said organelle and/or by transfection of a fluorescent or luminescent reporter gene in said organelle and/or by microinjection inside live cells of a luminescent or fluorescent marker or dye specifically taken up by said organelle.

All these techniques are well known by the man skilled in the art and some commercial kits are available for this type of labelling and should be used according to manufacturer's recommendations.

In a particular embodiment, mitochondria are labelled using calcein and colbat. Indeed, an operating procedure, known by the skilled person, to label mitochondria consists in the use of calcein being uploaded in living cell and restricted to the mitochondria by quenching the cytosolic fraction of calcein with cobalt (Petronilli et al., 1998).

Cells used in the method of the invention are living and isolated cells and are easily chosen by the skilled person depending on the exogenous element to be tested.

In an embodiment, cells used in the method of the invention are selected from the group consisting in cells from the organ suspected to be targeted by the exogenous element, cells from the organism in which effect is relevant or cells of a cell type which is particularly rich in organelles to be studied.

In an embodiment, cells used in the method of the invention are primary human cells isolated from various organs such as skin, muscle or liver, or are human cell lines such as HepG2, HEK293, NT2, lymphocyte cell lines or steroidogenic cell lines.

Cells used in the method of the invention are preferably selected from the group consisting of fibroblasts, blood cells, lymphocytes, dendritic cells, hepatic cells, muscle cells, kidney cells, neuronal cells, cells comprised in cell culture systems serving as skin substitute or co-culture systems. The term "co-culture system" refers, as used herein, to a culture system comprising more than one cellular type.

Preferably, non-transformed cells, such as non-immortalized cells, should be preferred allowing to obtain more easily transposable results to the in vivo situation, such as human situation.

The second step of the method of the invention, namely step b), consists of contacting isolated cells, as described above, and containing at least one labelled organelle to the exogenous element.

The third step of the method of the invention, namely step c), consists of determining variations of an organelle behaviour represented by at least two characteristics of at least one labelled organelle in the presence of the exogenous element.

These characteristics are selected from the group consisting of the motility, the morphology, the relationship with the cell cytoskeleton and the membrane permeability.

Preferably, variations of at least three characteristics are determined. More preferably, variations of the four characteristics are determined. The use of an increased number of characteristics to be determined allows increasing the accuracy of results obtained by the method of the invention, i.e. to improve the predictability of the effect of the exogenous element.

Variations of these characteristics are determined by reference to a control. This control may be a sample without any exogenous element, a sample with an element exhibiting a well-known effect such as an element with a known toxic effect or an element which has been proven to be non-toxic. Variations may also be determined in time such as before and after contact with the exogenous element.

Variations of the motility, the morphology, the relationship with the cell cytoskeleton and the membrane permeability of the labelled organelles are determined by any methods known by the skilled person.

In an embodiment, variations of the motility of a labelled organelle are determined by the measure of speed and/or amplitude and/or frequency of movements of this organelle.

Organelles are mobile within the cell cytoplasm. They move along the cell microtubule and actin filament network. Labelled organelles are observed in living cells and captured images are then analyzed.

The speed of an organelle' movements is measured by the displacement in μm of this organelle within the lapse of two captured frames. This measure is repeated over the total length of the image capture. Speed can be expressed as an average velocity observed for an organelle over the duration of the capture or by the maximal velocity observed for an organelle over the same duration.

The amplitude of organelle movements is expressed as a variable of the frequency of bursts in the total displacement of one organelle. A burst is defined as a sudden displacement within 30% of the maximal displacements of an organelle during the period of capture.

The frequency of organelle movements is expressed as a number of periods during which the organelle remains immobile.

In another embodiment, variations of the morphology of a labelled organelle are determined by observing the size of the organelle and/or the frequency of abnormal morphological pattern.

In a particular embodiment, the labelled organelle is mitochondria and variations of the morphology is determined by measuring the number of mitochondria affecting a particular morphology with respect to the total number of mitochondria in the cell and expressing this result in percent of the total mitochondria population or in number per $\mu m^2$. Measured parameters can include, but are not restricted to, the length of the mitochondria allowing for an appreciation of the equilibrium between fusion and fission, the number of mitochondria in a doughnut shape per cell, the number of mitochondrial derived vesicle per cell and the number of mitochondria undergoing swelling/aggregation per cell.

In another embodiment, variations of the relationship with the cell cytoskeleton are assessed by the directionality of the organelle with respect to the microtubules and/or actin filament network within the cell.

The concordance between the directionality of the organelle with that of the cytoskeleton is measured. This measure is first approximated with the measure of the area of entwined organelles to the total area of the cell and with the measure of the relative distance between the centroid of the region containing entwined organelles with respect to the centroid of the cytoplasmic microtubule organizing center. Both measures are correlated to the level of organization of the cytoskeleton and are used to scale the relationship of organelle organization with respect to that of the cytoskeleton.

When a measure suggests that the relationship between the mitochondria and the cytoskeleton may be altered, the integrity of the cytoskeleton is controlled using fluorescent-tubulin expressing cells or fluorescent-taxol treated cells to label microtubules and fluorescent phallacidin to label actin. Staining with fluorescence speckle microscopy may also be used when the dynamic of microtubule formation may be altered. Dual labelling with the organelle specific labelling techniques and the various labelling techniques for cytoskeleton components or their dynamic arrangements may be performed. The methodologies used are those known by the man of the art (Barak et al., 1980; Grego et al., 2001).

In another embodiment, variations of the membrane permeability are evaluated by the dynamic of the label leakage. The organelle label intensity is measured in time and the slope of the label leak into the cytoplasm is determined. In mitochondria, for instance, this leakage is aggravated when the mitochondria permeability transition pore (mPTP) is open.

All these variations are quantified as measured variables. These variables may be expressed in arbitrary units or in any unit which could be easily chosen by the skilled man. Each variable may be weighted in order to express the importance of the measured parameter.

In an embodiment, this third step comprises the follow-up in time and space of at least one signal emitted by the marker of at least one labelled organelle and the measure of at least one variable selected from the group consisting of the signal intensity, the signal pattern (i.e. the organelle shape), the signal displacement within the cell (i.e. the displacement of the organelle) and any type of calculated index of any two variables or their modification in time such as the ratio of intensities of different signals (e.g. signals from different markers).

In a preferred embodiment, the determination of variations of at least two characteristics of at least one labelled organelle in the presence of the exogenous element is performed by using a fluorescence microscope coupled to a Charge-Coupled Device (CCD) camera. Thus, in this embodiment, imaging and measurements are performed with this device.

In a particular embodiment, the determination of variations (i.e. imaging and measurements) of at least two characteristics, is performed in three spatial dimensions. The device to image and measure may therefore consist in a fluorescence microscope equipped with a motorized plate allowing the visualization of a sample in three dimensions. The CCD-camera allows the capture of high-resolution frames at high speed. The high content imaging procedure preferentially performed in the present invention allows the observation of organelles in their physiological context: the living cell. This procedure allows the elimination of experimental artefacts and thus potential biased results obtainable in studies on isolated organelles.

In another particular embodiment, the step c) of the method of the invention further comprises the recording and analysis of measured variables in a database.

The recording and analysis of these variables allows determining the behaviour of the labelled organelle which takes into account the motility, the morphology, the relationship to cytoskeleton and/or the membrane permeability of said organelle.

Therefore, in this embodiment, a recording and data management device may be used such as a computer in which an application allows to record, combine, analyze and quantify images observed through the microscope.

The content of the database is then analyzed to describe the different behaviours of a population of labelled organelles, within each image, according to at least one of the measured variables. Preferably, each image corresponds to an isolated cell.

In general, several cells from a single sample are imaged and the labelled organelles contained in the cells are followed. Several samples of the same cell type are generally studied.

Variations of an organelle's behaviour are defined by any significant difference in any of the measured variables between control condition and in presence of the exogenous element. The significance of potential differences is determined for each of the measured variables using an ANOVA.

The effect of an exogenous element is measured by incubating cells with various concentrations of this element and dose response effects are established through a post-hoc Bonferroni analysis.

In a particular embodiment, the measure of the mitochondrial motility, which by itself represents a phenotypic measure encompassing different molecular mechanisms contributing to mitochondrial functions, is representative of the mitochondrial function in its cellular context and thus constitute a mean of measuring these different mechanisms and their interaction with the other cellular events.

The mitochondrial motility depends on the mitochondrial bioenergetic regulation but also depends on calcium homeostasis, content of cellular ATP, level of cell phosphorylation, integrity of the cell microtubular system, and direct interaction of the mitochondria with the molecular motors. As such mitochondrial motility represents a composite measure of several mitochondrial functionalities within its cellular environment and constitutes an element of the mitochondrial behaviour.

In an embodiment, the measure of mitochondrial motility is used to prioritize and identify elements that present potential therapeutic value.

The fourth step of the method of the invention, namely step d), consists of determining cluster membership of the exogenous element. Clusters are established based on measures recorded in step c) and using reference elements and cluster membership is representative of the effect of the exogenous element on the organism.

Clusters may be established by performing steps a), b) and c) of the method of present invention on reference elements. These reference elements may be, for instance, molecules with well known effects or molecules of the same class of the exogenous element (e.g. anti-viral or anti-neoplastic drugs).

In order to determine cluster membership, the treatment of the measured variables consists in cluster analyses leading to the classification of the exogenous element in one of the clusters defined with variations of the organelle behaviour obtained with the reference elements.

To determine how the elements of the variable measured describing mitochondrial behaviour are relevant to the effect of reference elements, cluster analyses were performed using the Ward's method. The resulting cluster classification is used to determine cluster membership of the reference elements and any unknown elements which effect needs to be evaluated.

In a preferred embodiment, cluster membership is determined by taking into considerations all the measured variables as well as those related to the dose at which the first significant difference to the control condition is observed and the dose of the highest perturbation of organelle behaviour.

Such classification correlates with the effect of the exogenous element on the organism. Particularly, the classification obtained correlates with the level of dropout rates from treatments with the reference elements analyzed during clinical trials in humans. Indeed, the effect of this element is predicted to be as the effect of the reference elements contained in the same cluster. For instance, if the exogenous element belongs to a cluster comprising highly toxic substances, the predicted effect of this element is a high toxicity.

The cluster analysis of organelle motility, morphology, relationship to cytoskeleton as well as membrane permeability, more generally herein referred to as organelle behaviour, represents an integrative measure that can be interpreted as resulting from at least one or a combination of cellular events. For example, the changes in the typology of mitochondrial transport are correlated to various modifications of the level of intracellular calcium, to the depletion of cell ATP, to the interaction of mitochondria with motor specific ATPase, to the mitochondria bioenergetics or to the level of phosphorylation of cell proteins. Similarly, the changes in the mitochondrial morphology are also associated to various modifications of the level of intracellular calcium, to the depletion of cell ATP, to the interaction of mitochondria with motor specific ATPase, to the mitochondria bioenergetics or to the level of phosphorylation of cell proteins.

Moreover, it is correlated, in a dose-dependent or severity-dependent manner to disease state as well as to the manifestations of toxicity in an organism in which an exogenous element is applied. As such this analysis carries a high predictive value.

For example, ageing modifies the typology of mitochondrial motility in a way predictive of loss of cellular function over-time. Similarly, the poly-glutamine repeats insertion in the Huntington gene induces Huntington's disease that can be measured by a significant reduction in mitochondrial motility. Again, muscular dystrophy, related to loss of mitochondrial bioenergetics, can be modeled by the changes in the typology of mitochondrial behaviour showing modification of mitochondrial motility and morphology.

As a consequence the modifications of patterns in the mitochondrial behaviour indicate the development of a chronic dysfunctional state that could lead to pathologies such as neuronal degeneration, encephalopathy, muscular degeneration including cardiac myopathies, liver and kidney loss of function, lipodystrophies, pancreatitis, skin alterations, chronic pain, endocrine perturbations, whether induced by a pathological situation such as viral infections, cancer, cardio-metabolic diseases, muscular dystrophies, neurodegenerations and ageing, or by an exogenous element acting onto a healthy organism.

The effect, illustrated by the cluster membership, of an exogenous element can be compared to that of reference molecules of the same class or covering the same indication that may have for example induced a known chronic toxicity or that can be identified as a safe product.

The method of the invention may be used to predict the effect of an exogenous element on an animal or human organism In an embodiment, the method of the invention is used to predict the efficacy of an exogenous element on an animal or human organism. Preferably, the exogenous element is a drug and the efficacy is related to its capacity to improve the health of the organism in which the element is administered.

In another embodiment, the method of the invention is used to predict the toxicity of an exogenous element on an animal or human organism. Preferably, the exogenous element is a drug and the toxicity is related to deleterious effects of this drug on the health of the organism in which the element is administered.

In an embodiment, the method of the invention is used to predict the effect of an exogenous element on an animal or human organism, before or after the market introduction of said element. The method of the invention may be used to screen elements with therapeutic potential at any stage of their development, such as prior to their clinical development, before or after their market introduction.

The use of this method could thus sensibly reduce the cost of development of element with therapeutic potential for the pharmaceutical industry.

In a particular embodiment, the method of the invention is used to enhance the development of drugs for viral diseases (AIDS, Hepatitis), for cancers, for controlling cardio-vascular risks, for the management of metabolic diseases (like diabetes, for example), for muscular dystrophies (such as FSHD or BPCO, for example) and for neural degenerations (Alzheimer's disease, Parkinson's Disease, Huntington's Disease, Retinopathies).

The present invention finds its applications in numerous domains and is not restricted to the development of elements with therapeutic potential. It can be used to predict effect on the general health of any chemical substance such as used in the formulation of products such as cosmetic products, food and food supplements, products related to the production of additives in the industry, agriculture, environment and more generally in the chemical industry.

The method of the invention can be used to evaluate the impact on human health of any chemical products entering in the composition of common goods.

The following examples are given for purposes of illustration and not by way of limitation.

EXAMPLES

Example 1:

Prediction of Drug Toxicity

Cells were labelled with a mitochondrial dye such as mitotracker or were transfected with a GFP-expressing construct which expression was targeted to the mitochondria. Labelled mitochondria were observed in live cells using a fluorescence microscope. Time lapse images are captured and analyzed to record
- the typology of the mitochondria displacements by the measure of speed, amplitude and frequency of movements of individual mitochondria between two successive frames;
- the integrity of the mitochondrial membrane evaluated by the dynamic of the label leakage, aggravated when the mitochondrial permeability transition pore opens;
- the equilibrium of the relationship of the mitochondria with the cell cytoskeleton assessed by the directionality of the mitochondria with respect to the microtubules and/or actin filament network within the cell;
- the morphology adopted by the mitochondria measured by the length of the mitochondria and the frequency of the doughnut shapes observed. Doughnuts have been recognized as a morphological pattern adopted by mitochondria using electronic microscopy in various physiological or pharmacological conditions (Tasaka and Maeda, 1983; Evenson and Melamed, 1985).

Material and Methods

Living primary human fibroblasts containing mitochondria labelled with mitotracker green were incubated in the presence of 0.1 µM of imatinib mesylate for 30 minutes to 16 hours at 37° C. Images were captured for 20-40 frames every 3-15 sec on a z scale spanning 1 µm around the initial center of focus. Z slides were reconstructed to generate a movie that was further analyzed for mitochondrial tracking, shape recognition, length measurements and intensities measurements.

Measurement of the Variations of Membrane Permeability

Figure 1:
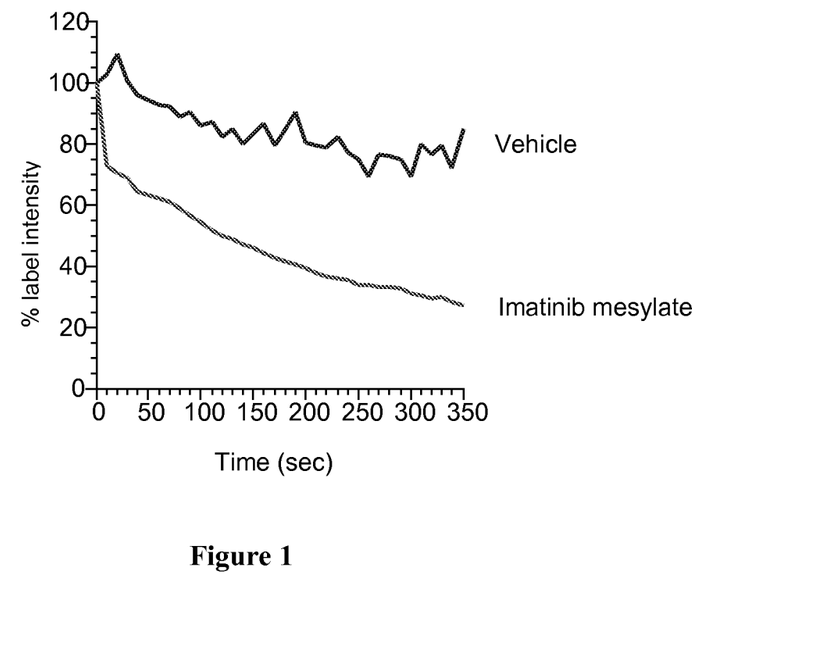
FIG. 1 shows a graph representing the quantification of the label leakage through opened mitochondrial permeability transition pore induced by incubation of cells with imatinib mesylate or only with the vehicle. Results are presented as a percent of label intensity as a function of time.

The contact of imatinib mesylate with cells containing labelled mitochondria resulted in a variation of the membrane permeability as illustrated by the dynamic of dye leakage resulting from mPTP opening (FIG. 1). This variation is the illustration of the loss of mitochondrial membrane integrity as effect of imatinib mesylate contact.

Measurement of the Variations of Mitochondrial Motility

Figure 2:
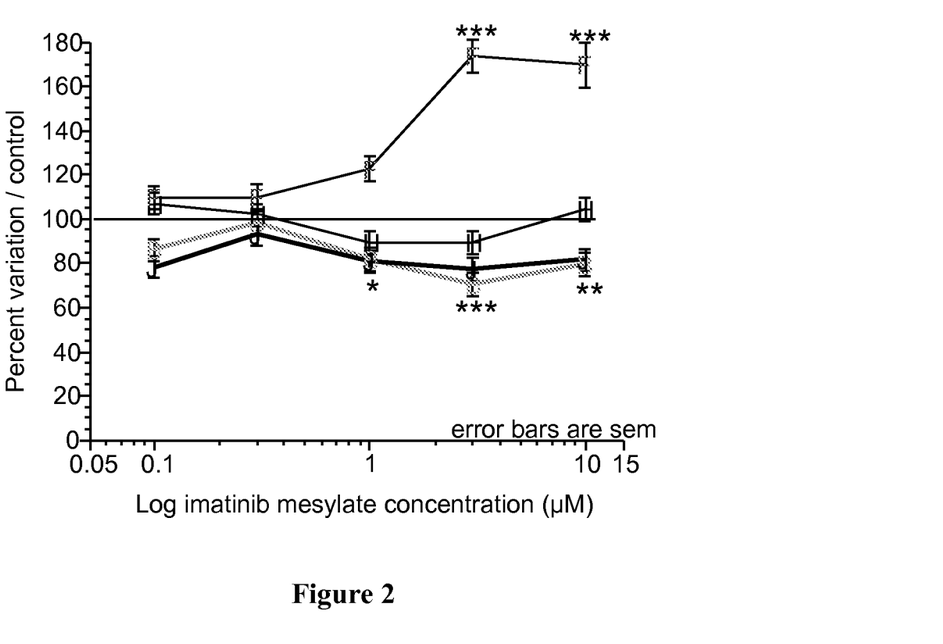
FIG. 2 shows a graph representing the effect of imatinib mesylate on mitochondrial motility. Measurements of mitochondrial displacement are recorded by the measure of periods of immobilization (F), burst frequency (H), maximal velocity (J) and average velocity (B) of individual mitochondria.

Mitochondrial displacement was assessed by the measure of the mitochondrial velocity, the amplitude of its movement and particularly the frequency of bursts and the frequency of movements represented by the periods of movement arrests (FIG. 2). All these measures were compared to the control conditions in which the cells were in the presence of the substance vehicle alone.

As shown in FIG. 2, imatinib mesylate induced variations of the mitochondrial motility, particularly increasing the number of immobilization periods of mitochondria.

Measurement of the Variations of Mitochondrial Relationship with the Cytoskeleton Changes in the relationship between the mitochondria and the cell cytoskeleton are observed by assessing the directionality of the mitochondria along the general orientation of the microtubule network. Areas containing entwined mitochondria are determined with respect to the total cell area and expressed as a percent.

Imatinib mesyalte did not induce any variation of mitochondrial relationship with the cytoskeleton (data not shown). However, some other tested compounds affected this relationship.

Figure 4:
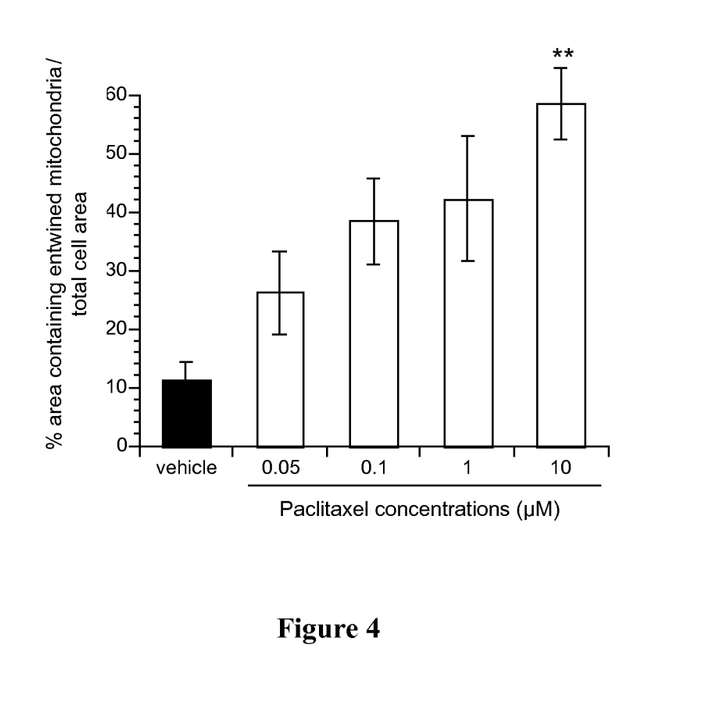
FIG. 4 shows variations of mitochondrial relationship with the cytoskeleton induced by paclitaxel. Measures of area containing entwined mitochondria (in percent of the total cell area) are represented as a function of the paclitaxel concentration.

For example, as shown in FIG. 4, paclitaxel affected the relationship of mitochondria with cytoskeleton in a dose-dependent manner and thus affected the mitochondrial behaviour.

This molecule is known to alter the dynamic of microtubule assembly by stabilizing the microtubule network. In this example, the inventors demonstrated that modulating cytoskeleton dynamics affects the mitochondrial behaviour as measured by the tightness between mitochondrial directionality with the general orientation of microtubules within the cell cytoplasm.

Measurement of the Variations of Mitochondrial Morphology

Changes in mitochondrial morphology, i.e. in the mitochondria length and in the formation of doughnuts, were observed associated with compound toxicity in a dose dependent manner.

The mitochondria length and the formation of doughnuts are two parameters which indicate the dynamic modulation of the fission-fusion phenomenon that occurs in the mitochondria. When very short, the mitochondria cannot assume a doughnut shape anymore, thus making the loss of the doughnut shapes a signal very significant of a toxicity than cannot be compensate by the fission-fusion dynamics. When the equilibrium of fission-fusion is impaired the fragmentation of the mitochondria is associated with neurodegeneration (Knott et al., 2008).

Figure 3A:
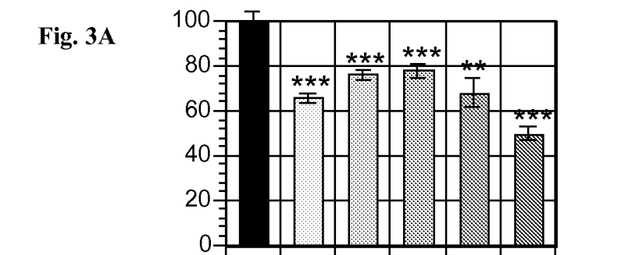
FIG. 3 shows a graph representing the effect of imatinib mesylate on the morphology of mitochondria. Variations (in percent of the vehicle) in the mitochondria length (FIG. 3A) and in the formation of doughnuts (FIG. 3B) are represented as a function of the dose of the substance (Vehicle only, 0.1 µM, 0.3 µM, 1 µM, 3 µM and 10 µM of imatinib mesylate).
Figure 3B:
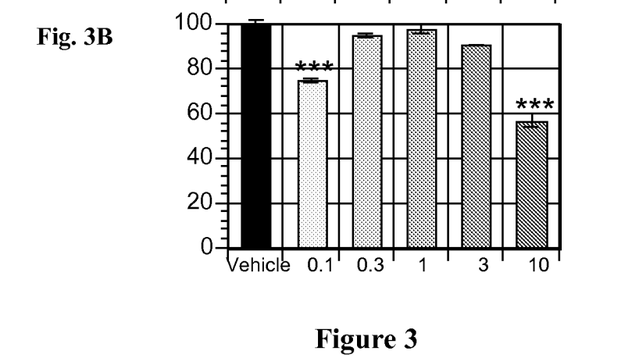

As shown in FIG. 3, imatinib mesylate induced variations for mitochondria length (FIG. 3A) and the formation of doughnuts (FIG. 3B).

Calculation of the Toxicity Index Using the Different Variables Describing the Mitochondrial Behaviour and Cluster Analysis Measurements of variations of the mitochondria behaviour induced by 11 exogenous substances were performed as exemplified above for the imatinib mesylate and Paclitaxel.

17 different variables obtained thought these measurements and describing the effect of 11 exogenous substances used at different doses (at least 4 from 0.05 µM to 10 µM), were simultaneously recorded on live cells in which mitochondria were labelled. These variables included all the variables measured on the 4 dimensions of the mitochondrial behaviour plus those related to dosage information such as the maximal dose tested and the dose at which the maximal effect was recorded. The inventors also included a variable recording loss of mitochondrial label independent from mPTP opening.

Reference compounds used in this example contained molecules with known mitochondrial toxicity (Zidovudine, Lamivudine, Doxorubicin) and compounds which mechanism of toxicity did not directly impact the mitochondria (Docetaxel, Paclitaxel, Cisplatine). The exogenous substances used contained molecules which toxicity was recognized at different stage of clinical development (BILN-2063, Nocodazole, Nevirapine, Effavirenz) and molecules which toxicity was only recognized post-marketing (Gleevec (imatinib mesylate), Vioxx).

Results

Figure 5:
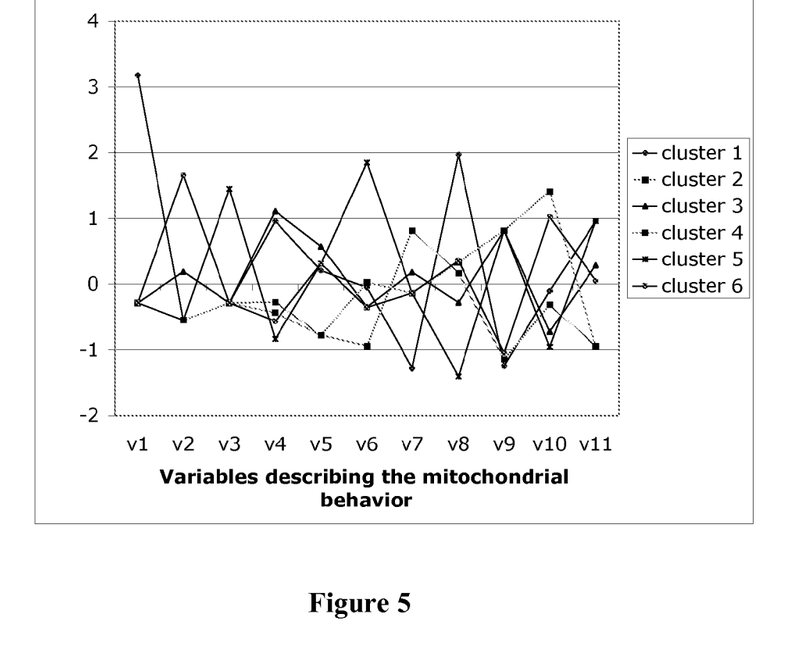
FIG. 5 shows the Z scores of the different cluster group with respect to the 11 variables measured describing the mitochondrial behaviour.

The different variables used to qualify the mitochondrial behaviour and the effect of various doses of exogenous substance on this behaviour were first classified into 9 different dimensions corresponding to the most significant variations of the four mitochondrial behaviour dimensions and to dose dimensions (e.g. the dose inducing the maximum effect or the lower dose inducing a significance variation), using cluster analyses with the weighted pair-group centroid method. The performances of 11 different exogenous substances within the anti-viral, anti-inflammatory and anti-neoplastic classes of molecules were then analyzed using cluster analyses with Ward's method (Ward, 1963). This analysis resulted in the segregation of the compounds into different clusters that allowed the inventors to classify and compare the compounds within one another with respect to their toxicity potential. In this example, 6 different groups were found (FIG. 5).

From this analysis the clusters could be organized into a hierarchy based on the type and amplitude of the impairments induced by the exogenous substances on the mitochondrial behaviour. This classification is shown below:

Cluster 1>Cluster 5>Cluster 4>Cluster 3>Cluster 6>Cluster 2

To explore the relationship between the different types of effects of the exogenous substances on the impairment of mitochondrial behaviour (cluster membership) and the toxicity of exogenous substances (known from the literature) a discriminate analysis was performed. More than 83% of the original group cases were correctly classified.

For instance, imatinib mesylate belongs to the cluster 5 and was thus predicted to exhibit a relatively high toxicity. Having submitted this molecule to the method of the invention prior to clinical development could have warned its developer of the risk of chronic mitochondrial impairment that could lead to cardio-toxicity, hence allowing for further optimization of the molecule prior to its clinical development.

Example 2:

Prediction of Drug Efficacy

Prediction of the Efficacy of a Drug for the Treatment of Huntington's Disease.

Figure 6:
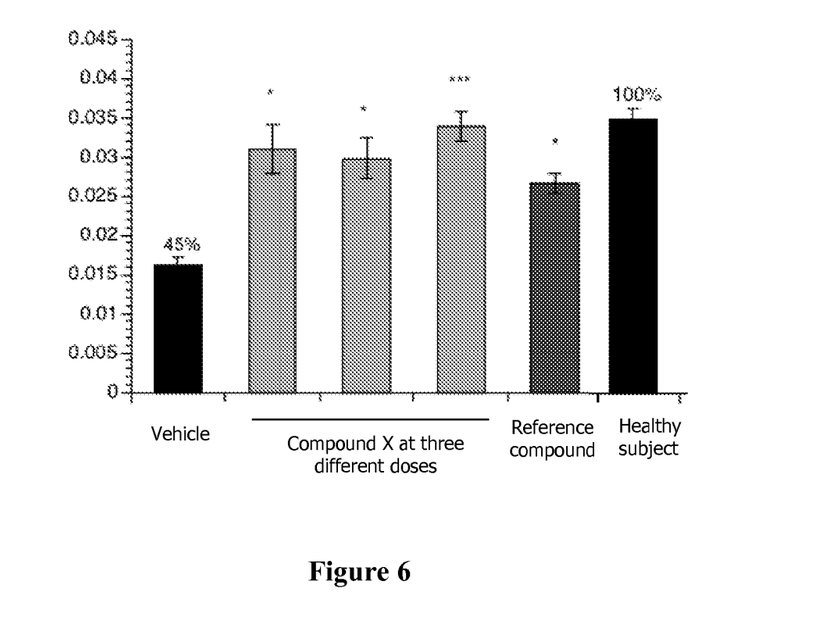
FIG. 6 shows a graph representing indexes of mitochondrial behaviour obtained from Huntington's disease patient cells incubating with the vehicle (vehicle), Huntington's disease patient cells incubating with three different doses of the compound X, Huntington's disease patient cells incubating with a reference compound and healthy subject cells incubating with the vehicle.

Healthy subjects and patients suffering from Huntington's disease were studied (at least 6 in each group). These were age and gender matched but varied in the disease progression and severity at the time of tissue sampling. The data showed a significant defect induced by the disease in the mitochondrial behaviour as represented by the index of the mitochondrial behaviour obtained from patient cells incubated with the vehicle compared to the index obtained from healthy subject cells (FIG. 6).

The method of the invention was used to test the efficacy of molecules under development to reverse/compensate for this behavioural impairment of mitochondria functionality. The inventors found a particular undisclosed compound (compound X) that was particularly efficacious in restoring mitochondrial behaviour characteristics of HD-affected cells to the level of that seen in cells originating from healthy subjects. The efficacy of the compounds was compared to that of a compound known to reduce neuronal loss in a model of rat primary neurons in which the mutation of the Huntingtin gene was mimicked (FIG. 6, reference compound). To date, no treatment exists for Huntington's disease.

The mitochondrial behaviour characteristics were represented as an index (or a score), which was representative of the effect determined by measuring variables of mitochondrial characteristics.

The compound X was tested to show a therapeutic effect on Huntington disease.

As shown in FIG. 6, the compound X exhibited a higher index than the reference compound at a lower tested dose and thus could be considered more efficacious and more potent.

These results demonstrate that the compound X is predicted to have a therapeutic effect for Huntington disease treatment and is thus a good candidate for subsequent steps in drug development.

Prediction of the Efficacy of an Anti-Age Formula

Figure 7A:
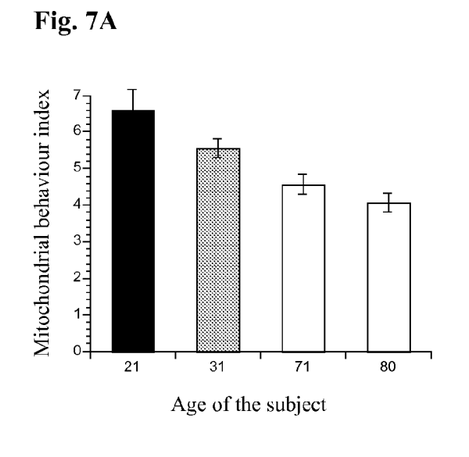
FIG. 7A shows a graph representing mitochondrial behaviour indexes obtained with cells from subjects who are 21, 31, 71 or 80.

The inventors have shown that the measurements of mitochondrial behaviour characteristics could model the loss of mitochondrial functionality during ageing (FIG. 7A).

Healthy subjects were analyzed. Each age group represented a minimum of 3 subjects. All subjects were of the feminine gender.

Figure 7B:
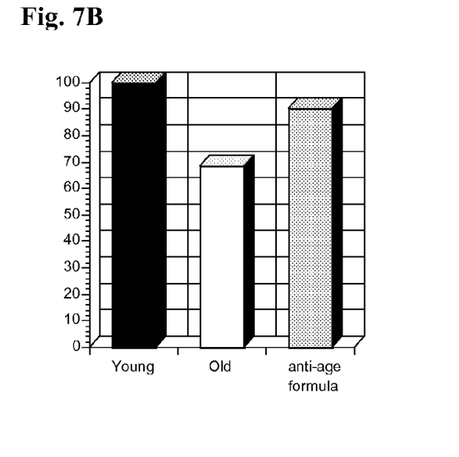
FIG. 7B shows a graph representing indexes of mitochondrial behaviour obtained with cells from a young subject, from an old subject and with cells from an old subject which have been incubated with an anti-age formula.

An anti-age formula was tested with the method of the present invention and it was demonstrated that this formula allowed to restore, at least in part, the mitochondrial behaviour characteristics of old cells (FIG. 7B).

Using the method of the invention, compounds suspected to have anti-age properties could then be tested by comparing results obtained with cells of a young subject to cells of an older subject. Effective compounds will obliterate or reduce the significant difference in mitochondrial behaviour observed between young and old subjects.

References

Amacher D. E., "Drug-associated mitochondrial toxicity and its detection", Curr. Med. Chem., 2005, 12(16):1829-39;

Barak et al., (1980) "Fluorescence Staining of the Actin Cytoskeleton in Living Cells with 7-Nitrobenz-2-Oxa-1,3-Diazole-Phallacidin", PNAS (USA), 77(2):980-984;

Dykens J A, Will Y. The significance of mitochondrial toxicity testing in drug development. Drug Discov Today. 2007 September; 12:777-85;

Evenson D. P. and Melamed M. R. "Rhodamine 123 Alters the Mitochondrial Ultrastructure of Cultured L1210 Cells", The Journal of Histochemistry and Cytochemistry, 33 (4): 353-359 (1985);

Gustavson K. E. et al., "Comparisons of human-cell-based and submitochondrial particle bioassay responses to the MEIC compounds in reference to human toxicity data", Toxicology. 2002 Aug. 15; 177(2-3):131-42;

Grego et al., (2001) "Microtubule treadmilling in vitro investigated by fluorescence speckle and confocal microscopy", Biophysical J. 81, 66-78;

Ishikawa T. et al., "Effects of therapeutic agents on cellular respiration as an indication of metabolic activity", Human Exp. Toxicol., 2006 March, 25(3):135-140;

Jones et al., "Randomized Phase III Study of Docetaxel Compared With Paclitaxel in Metastatic Breast Cancer", J Clin Oncology; 23 (24):5543-5551; (August 2005);

Kerkela R. et al., "Cardiotoxicity of the cancer therapeutic agent imatinib mesylate", Nat Med. 2006 August; 12(8):908-16;

Knott et al., "Mitochondrial fragmentation in neurodegeneration." Nat Rev Neurosci.;9(7):505-18 (2008 July);

Petronilli V, et al., Imaging the mitochondrial permeability transition pore in intact cells. 1998, Biofactors. 8(3-4):263-72;

Seok S. H. et al., "Arsenite-induced apoptosis is prevented by antioxydants in zebrafish liver cell line", Toxicol. In Vitro, 2007 August, 21(5):870-7;

Tasaka M. and Maeda Y. "Ultrastructural Changes of the Two Types Of Differentiated Cells during the Migration and Early Culmination Stages of —Dictyostelium discoideum"; Develop Growth and Differ; 25 (4), 353-360 (1983);

Ward, Joe H. "Hierarchical grouping to optimize an objective function". Journal of the American Statistical Association, March 1963, vol. 58, no. 301, p. 236-244;

Will Y. et al., "*Analysis of mitochondrial function using phosphorescent oxygen-sensitive probes*", Nat. Protoc., 2006, 1(6):2563-72.

The invention claimed is:

1. An in vitro method to predict the effect of an exogenous element on an animal or human organism comprising:
    a) labelling at least one organelle contained in animal or human isolated cells;
    b) contacting said isolated cells containing said at least one labelled organelle with said exogenous element;
    c) measuring variations of organelle behaviour in said isolated cells represented by four characteristics of said at least one labelled organelle in the presence of said exogenous element, said four characteristics being motility, morphology, relationship with the cell cytoskeleton and membrane permeability, the variations of at least two of these characteristics being determined in three spatial dimensions; and
    d) determining cluster membership of said exogenous element, clusters being established using reference elements and being based on all variations recorded in step c), said cluster membership being representative of the effect of said exogenous element on said organism, thereby predicting the effect of said exogenous element on said animal or human organism.

2. The method according to claim 1, wherein variations of the motility of said at least one labelled organelle are determined by the measure of speed and/or amplitude and/or frequency of movements of said organelle.

3. The method according to claim 1, wherein variations of the morphology of said at least one labelled organelle are determined by observing the size of the organelle and/or the frequency of abnormal morphological pattern.

4. The method according to claim 1, wherein variations of the relationship with the cell cytoskeleton of said at least one labelled organelle are determined by observing the directionality of said organelle with respect to the microtubules and/or actin filament network within the cell.

5. The method according to claim 1, wherein variations of the membrane permeability of said at least one labelled organelle are determined by the dynamic of the label leakage.

6. The method according to claim 1, wherein said at least one organelle is labelled with a marker emitting fluorescent or luminescent signal.

7. The method according to claim 6, wherein said at least one organelle is labelled using a fluorochrome specific of said organelle and/or by transfection of a fluorescent or luminescent reporter gene in said organelle and/or by microinjection in the cell of a luminescent or fluorescent marker specifically taken up by said organelle.

8. The method according to claim 1, wherein said at least one organelle is selected from mitochondria, vesicles and/or peroxisomes.

9. The method according to claim 8, wherein said at least one organelle is mitochondria.

10. The method according to claim 9, wherein said mitochondria is labelled using calcein and cobalt.

11. The method according to claim 1, wherein step c) comprises the follow-up in time and space of the signal emitted by a marker in said at least one organelle and the measure of at least one variable selected from the group consisting of the signal intensity, the signal pattern, the signal displacement within the cell and the ratio of intensity of different signals.

12. The method according to claim 11, wherein step c) further comprises the recording in a database and analysis of measured variables.

13. The method according to claim 12, wherein step c) is performed by using a fluorescence microscope coupled to a charge coupled device (CCD) camera.

14. The method according to claim 13, wherein step c) comprises determining said variations of said at least two characteristics in three spatial dimensions.

15. The method according to claim 1, wherein the exogenous element is selected from a physical particle, a wave and a chemical or biological substance.

16. The method according to claim 15, wherein said exogenous element is selected from a drug authorized to be marketed, a biological or chemical substance with therapeutic potential, a biological or chemical substance contained in drugs, fertilizers, phytochemical products, food, cosmetic products and/or environmental toxicants.

17. The method according to claim 1, wherein said isolated cells are selected from fibroblasts, blood cells, lymphocytes, dendritic cells, hepatic cells, muscle cells, kidney cells, neuronal cells, cells comprised in cell culture systems used as skin substitute and/or co-culture systems.

18. The method according to claim 1, used to predict the efficacy of an exogenous element on an animal or human organism.

19. The method according to claim 1, wherein the effect is the toxicity of the exogenous element on the animal or human organism.

20. The method according to claim 1, used to predict the effect of an exogenous element on an animal or human organism, before or after the market introduction of said element.

21. The method according to claim 1, wherein said exogenous element is a drug.

22. The method according to claim 14, wherein determining said variations of said at least two characteristics in three spatial dimensions is performed by a fluorescence microscope equipped with a motorized plate allowing the visualization of a sample in three dimensions and said fluorescence microscope is coupled to a CCD camera.

* * * * *

UNITED STATES PATENT AND TRADEMARK OFFICE
CERTIFICATE OF CORRECTION

PATENT NO. : 8,497,089 B2
APPLICATION NO. : 12/675494
DATED : July 30, 2013
INVENTOR(S) : Nathalie Compagnone

It is certified that error appears in the above-identified patent and that said Letters Patent is hereby corrected as shown below:

In the Specification

Column 1,
Line 65, "(Gustayson" should read --(Gustavson--.

Column 13,
Line 19, "Cluster 4>" should read --Cluster 4≥--.

Signed and Sealed this
Twenty-sixth Day of November, 2013

Margaret A. Focarino
*Commissioner for Patents of the United States Patent and Trademark Office*